(12) United States Patent
Peter

(10) Patent No.: US 8,653,464 B2
(45) Date of Patent: Feb. 18, 2014

(54) COMBINATION OF SINGLE PHOTON EMISSION COMPUTED TOMOGRAPHY AND OPTICAL IMAGING DETECTOR

(75) Inventor: Joerg Peter, Heiligkreuzsteinach (DE)

(73) Assignee: Deutsches Krebsforschungszentrum Stiftung des Oeffentlichen Rechts, Heidelberg (DE)

( * ) Notice: Subject to any disclaimer, the term of this patent is extended or adjusted under 35 U.S.C. 154(b) by 782 days.

(21) Appl. No.: 12/681,839

(22) PCT Filed: Oct. 10, 2008

(86) PCT No.: PCT/EP2008/063617
§ 371 (c)(1),
(2), (4) Date: Apr. 6, 2010

(87) PCT Pub. No.: WO2009/047328
PCT Pub. Date: Apr. 16, 2009

(65) Prior Publication Data
US 2010/0219348 A1    Sep. 2, 2010

Related U.S. Application Data

(60) Provisional application No. 60/960,731, filed on Oct. 11, 2007.

(51) Int. Cl.
*G01T 1/166* (2006.01)
*G01T 1/00* (2006.01)

(52) U.S. Cl.
USPC ............... 250/363.1; 250/363.04; 250/394

(58) Field of Classification Search
USPC .......... 250/363.04, 363.1, 505.1, 363, 4, 394
See application file for complete search history.

(56) References Cited

U.S. PATENT DOCUMENTS

| 2005/0215873 | A1 | 9/2005 | Peter |
| 2006/0113482 | A1* | 6/2006 | Pelizzari et al. ......... 250/370.09 |
| 2007/0034804 | A1* | 2/2007 | Danzer et al. .................. 250/347 |
| 2009/0032714 | A1* | 2/2009 | Peter et al. ............... 250/363.01 |

FOREIGN PATENT DOCUMENTS

| EP | 1700568 | * | 9/2006 |
| WO | WO 2006/111486 A1 | | 10/2006 |

OTHER PUBLICATIONS

Peter et al., "PET-MOT—A Novel Concept for Simultaneous Positron and Optical Tomography in Small Animals," 2005 IEEE Nuclear Symposium Conference Record, p. 1757-1760.*

(Continued)

*Primary Examiner* — David Porta
*Assistant Examiner* — Yara Green
(74) *Attorney, Agent, or Firm* — Muncy, Geissler, Olds & Lowe, PLLC

(57) ABSTRACT

The invention relates to an imaging method for simultaneously determining in vivo distributions of bioluminescent and/or fluorescent markers and radioactive markers at identical projection angles, the distribution of the bioluminescent and/or fluorescent markers being determined by separate detection of photons having a first average energy, which are emitted by the bioluminescent and/or fluorescent markers, by means of at least one first detector and the distribution of the radioactive markers being determined by simultaneous separate detection of photons having a second average energy, which are emitted by the radioactive markers, by means of at least one second detector. Furthermore, it also relates to an apparatus for carrying out the imaging method, containing at least one micro lens array optical tomographic imaging system as first detector, at least one single photon emission computer tomography (SPECT) detector as second detector.

10 Claims, 7 Drawing Sheets

(56) References Cited

OTHER PUBLICATIONS

Celentano et al., "Preliminary Tests of a Prototype System for Optical and Radionuclide Imaging in Small Animals," IEEE Transactions on Nuclear Science, vol. 50, No. 5, Oct. 2003, pp. 1693-1701.*

Joerg Peter et al.: "Development and Initial Results of a Tomographic Dual-Modality Positron/Optical Small Animal Imager", IEEE Transactions on Nuclear Science, vol. 54, No. 5, Oct. 1, 2007, pp. 1553-1560.

Prout et al.: "Detector Concept for OPET, a Combined PET and Optical Imaging System", IEEE Nuclear Science Symposium and Medical Imaging Conference, Portlan, OR, Oct. 19-25, 2003, vol. 4, pp. 2252-2256.

Peter et al.: "Development and Initial Results of a Dual-Modality SPECT/Optical Small Animal Imager", Nuclear Science Symposium Conference Record, Puerto Rico Oct. 23-29, 2005, vol. 4, Oct. 23, 2005, pp. 1969-1972.

* cited by examiner

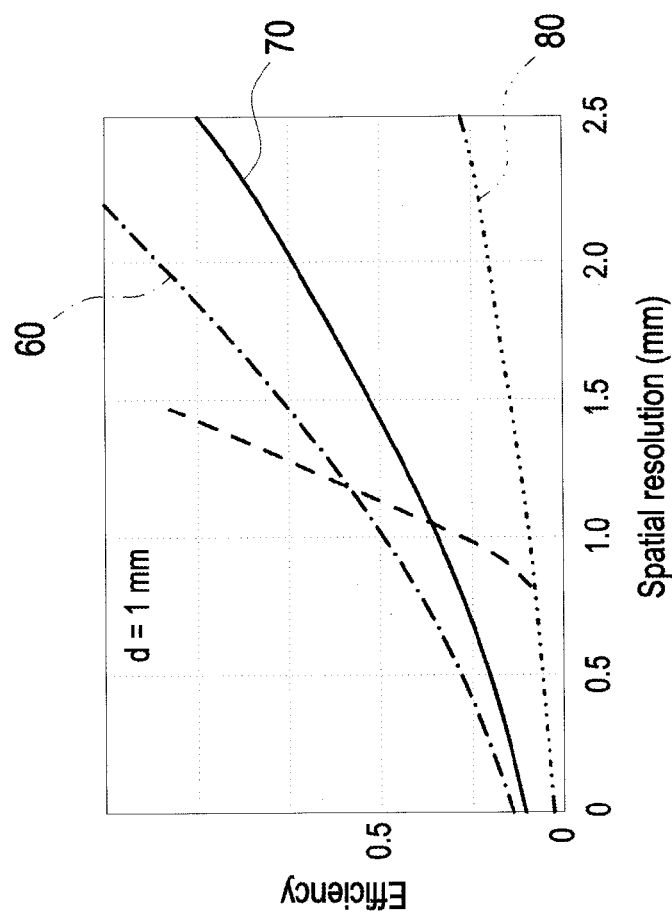
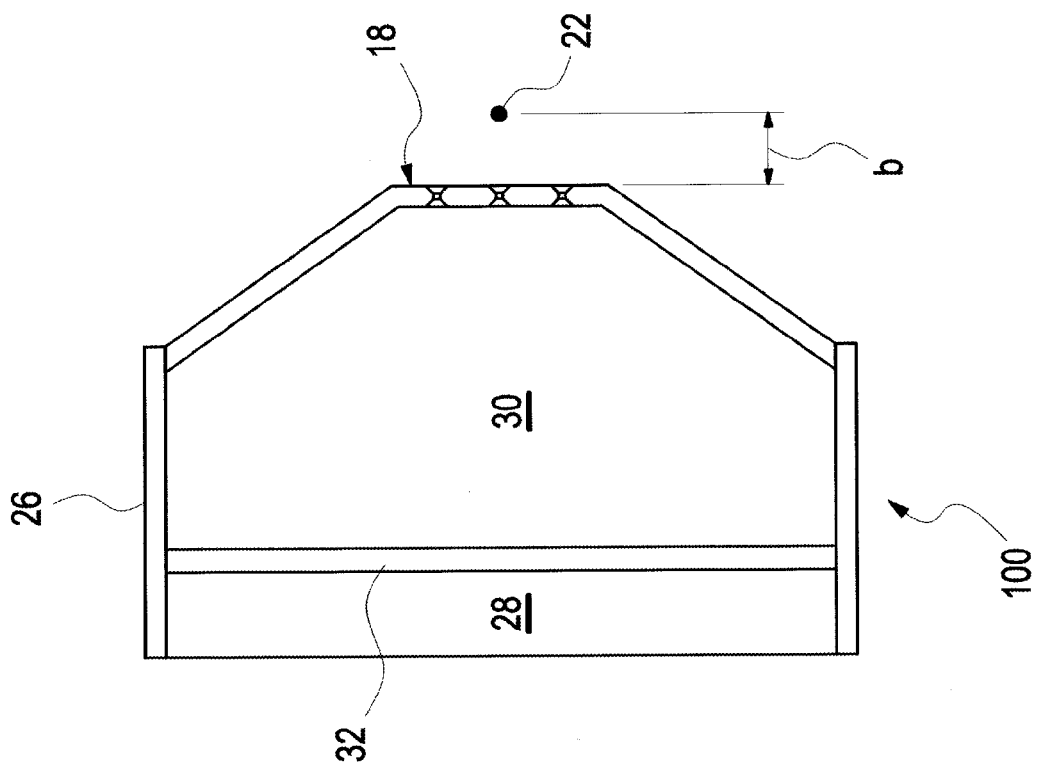
Fig. 3

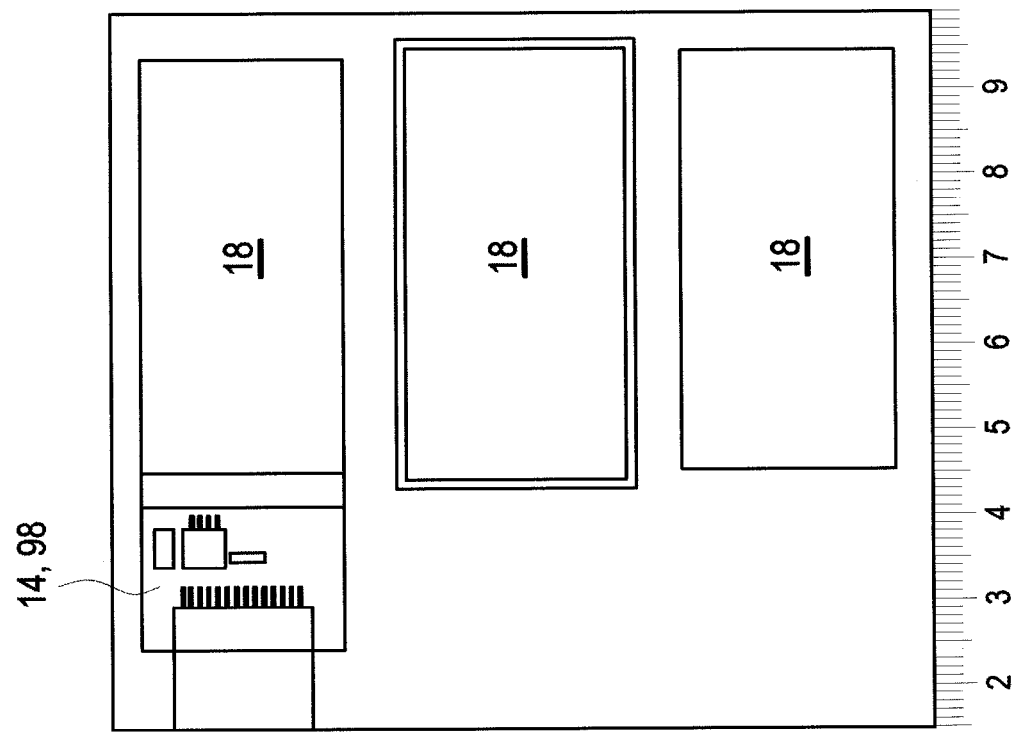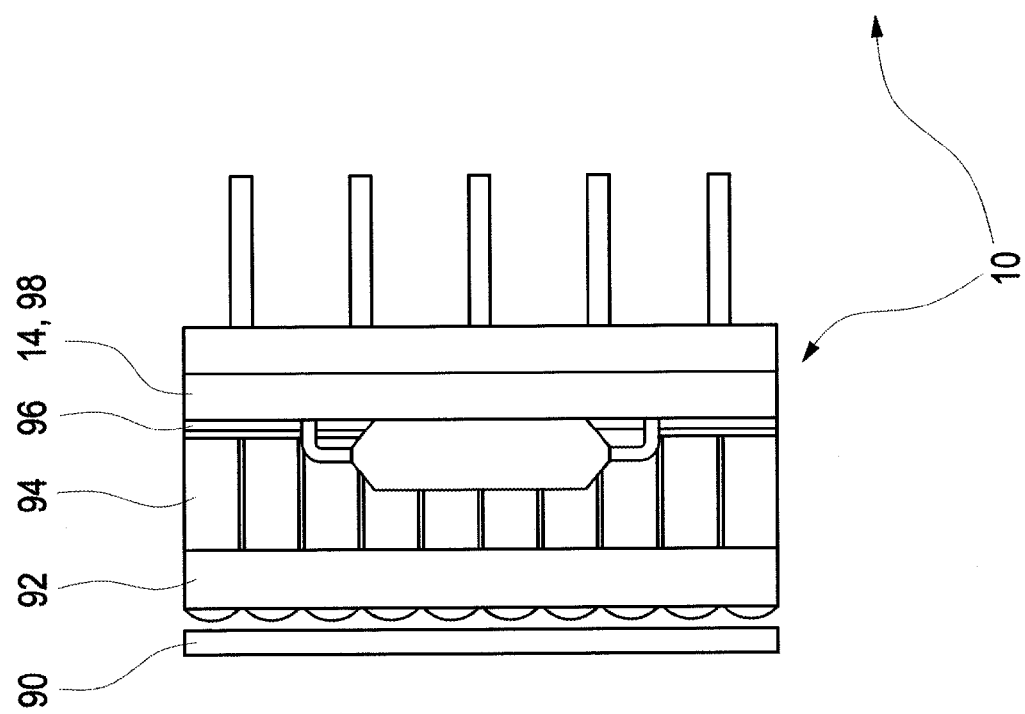
Fig. 4

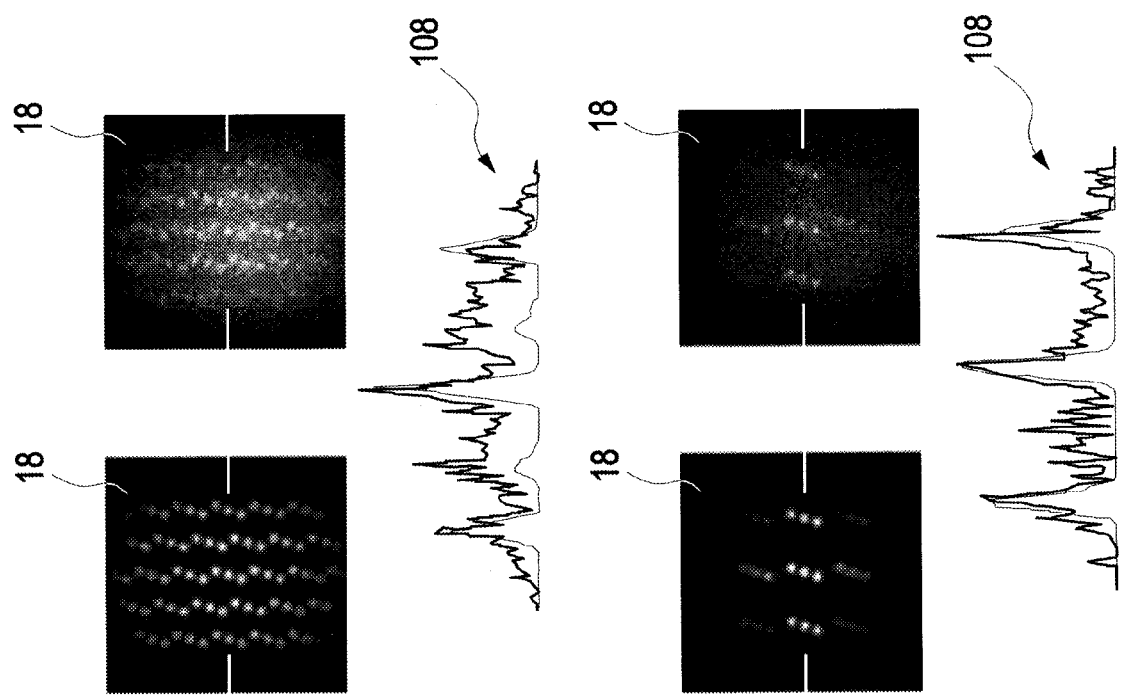
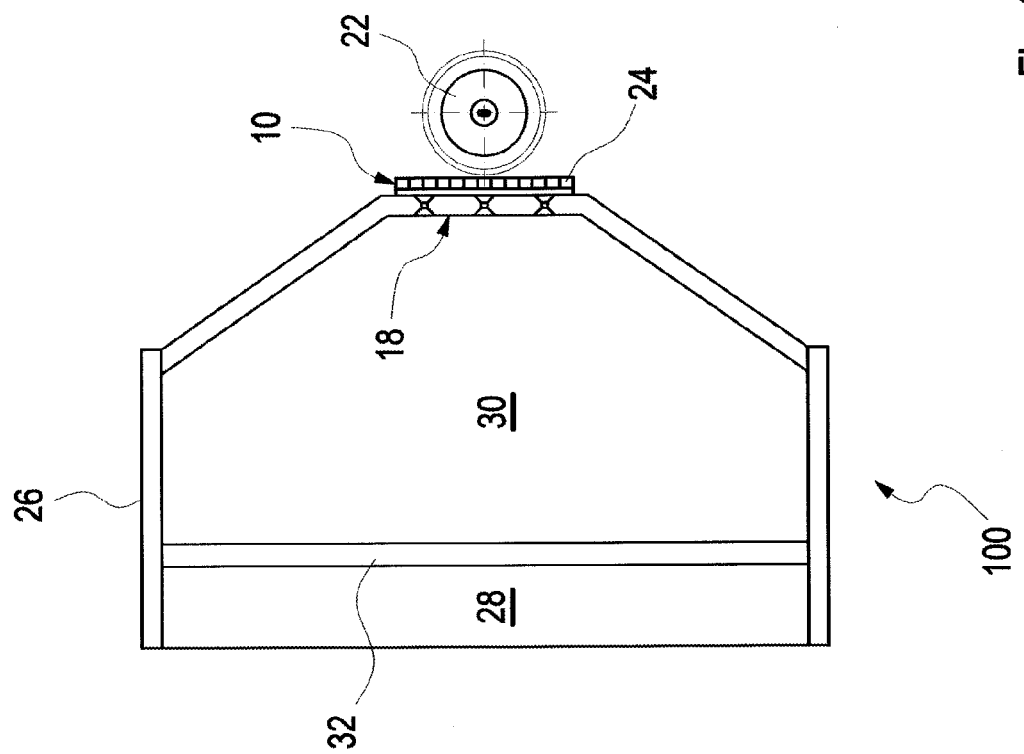
Fig. 6

COMBINATION OF SINGLE PHOTON EMISSION COMPUTED TOMOGRAPHY AND OPTICAL IMAGING DETECTOR

This application is a national stage of International Application No.: PCT/EP2008/063617, which was filed on Oct. 10 2008, and which claims priority to U.S. Provisional Application No.: 60/960,731, which was filed in the US on Oct. 11, 2007, and which are both herein incorporated by reference.

FIELD OF THE INVENTION

The field of the present invention concerns an integrated, highly sensitive, and non-invasive SPECT and OT imaging system.

BACKGROUND

Single photon emission computed tomography (SPECT) is a non-invasive imaging system for detecting photons that are emitted from a radioactive substance, such as a molecular probe, that has been administered to an individual. Clinically, SPECT is useful in oncology for determining, grading, and locating tumor mass and evaluating its malignancy before and after treatment. Radio labeled probes produce a continuous signal, independent of any underlying molecular interaction via radioisotope decay.

Optical planar imaging/tomography (OT) is an alternative noninvasive and nonhazardous molecular imaging system, which detects light that is propagated through a tissue at single or multiple projections. Fluorescence mediated optical imaging can localize and quantify fluorescent probes present in tissues at high sensitivities and at millimeter resolutions, which make it a very useful tool for imaging breast cancer, brain function and gene expression in vivo. Optical imaging uses activatable probes that produce detectable signals upon interaction with a target.

The present invention is drawn to a combination of SPECT and OT systems whereby the SPECT system is equipped with any type of known collimator (in case of small animal imaging a multi-pinhole type is used most effectively and used in the following exemplarily as one possible embodiment) and the OT system is of very thin extension and allocated within the field-of-view of the SPECT camera and between the imaged object and the SPECT collimator.

Since both regional distribution and time variation of the underlying multivariate photon distributions are acquisition and subject specific and diversified by variations thereof, and imaging procedures cannot be performed repeatedly at short time intervals on the same living object in many cases, combined and simultaneous imaging is needed and possible with this novel device carrying clearly advantageous potential. Further advantages are simultaneous recording of tracer kinetics, less subject encumbrance, and identical imaging geometries. The proposed nuclearoptical tomographic imaging system has the potential to accurately quantify fluorescence and bioluminescence in deep heterogeneous media in vivo. The inventive apparatus supports the development of generalized reporter probes.

SUMMARY

An aspect of the present invention is a dual-modality imaging system, wherein at least one single photon emission computed tomography (SPECT) camera for acquiring SPECT data and at least one optical imaging detector for acquiring optical imaging data are arranged to acquire the SPECT data and the optical imaging data of an imaged object simultaneously and from the same projection angle, the at least one optical imaging detector being a non-contact optical imaging detector for bioluminescence, fluorescence, and reflectance imaging and wherein the SPECT subsystem apparatus comprises a SPECT-detector to which, be way of example, a multipinhole collimator is attached for high-resolution/high-sensitivity radio-nuclide imaging and at least one optical imaging detector being arranged within the imaging volume to detect photons emitted by the imaged object, characterized in that the at least one optical imaging detector comprises a micro-lens array with a plurality of micro-lenses, the optical detector being attached onto the surface of the multi-pinhole collimator of the SPECT system.

An another aspect of the present invention is a dual-modality imaging system, comprising (1) at least one single photon emission computed tomography (SPECT) camera for acquiring SPECT data, which comprises a SPECT-detector to which a collimator is attached and (2) at least one optical imaging detector for acquiring optical imaging data which is placed between the imaged object and the SPECT camera.

In one embodiment, the SPECT camera collimator is a single-pinhole type, or is a multi-pinhole type, or is a parallel beam type, or is a fan-beam type, or is a conbeam type, or is an astigmatic collimator type, or is any parallel, diverging, or converging multi-hole type, or is an converging type with a single or multitude of focal points or lines.

In another embodiment, the optical imaging detector is closely attached at the imaged object facing front of the collimator of the SPECT apparatus, the collimator preferably being a multi-pinhole type (see FIG. 2).

In another embodiment, the optical imaging detector is placed at a certain distance to the imaged object facing front of the collimator of the SPECT apparatus, the collimator preferably being a fan-beam or cone-beam type (see FIG. 7).

In another embodiment, the optical imaging detector is placed at a certain shorter distance to the imaged object independently of the SPECT apparatus while the SPECT apparatus is placed at a certain longer distance to the optical imaging detector.

In another embodiment, an optical imaging detector comprises at least one photo detector.

In another embodiment, an optical imaging detector comprises a position-sensitive photo detector.

In another embodiment, an optical imaging detector comprises a micro-lens array and the position-sensitive photo-detector is positioned at the focal plane of a micro-lens array.

In one embodiment, the position-sensitive photo-detector is at least one sensor selected from the group of charge-coupled device (CCD) based detector, avalanche photo diode (APD) array, photo diode array or complementary metal-oxide semiconductor (CMOS) sensor.

In further embodiment, the SPECT-detector and the optical imaging detector are mounted on a common gantry which is rotatable around 360 degrees to allow for arbitrary radial positioning of the optical detector and of the SPECT camera and to allow for tomographic imaging.

In one embodiment, an apparatus of the present invention comprises a single or plurality of light sources for illuminating the imaged object.

BRIEF DESCRIPTION OF THE DRAWINGS

FIG. 3: shows the apparatus and results of a study illustrating the improvement of the performance of the SPECT-detector if multi-pinhole collimators are used. Shown are the results for 1, 4, and 6 pinholes with regard to sensitivity.

FIG. 4: shows a rendering of the cross-sectional view of the optical detector along with a photograph of the various parts of the detector.

FIG. 6: shows the result of Monte Carlo simulations performed to investigate the multi-pinhole setup and possible effects the optical sensor might have on the SPECT photons.

DETAILED DESCRIPTION

Figure 1:
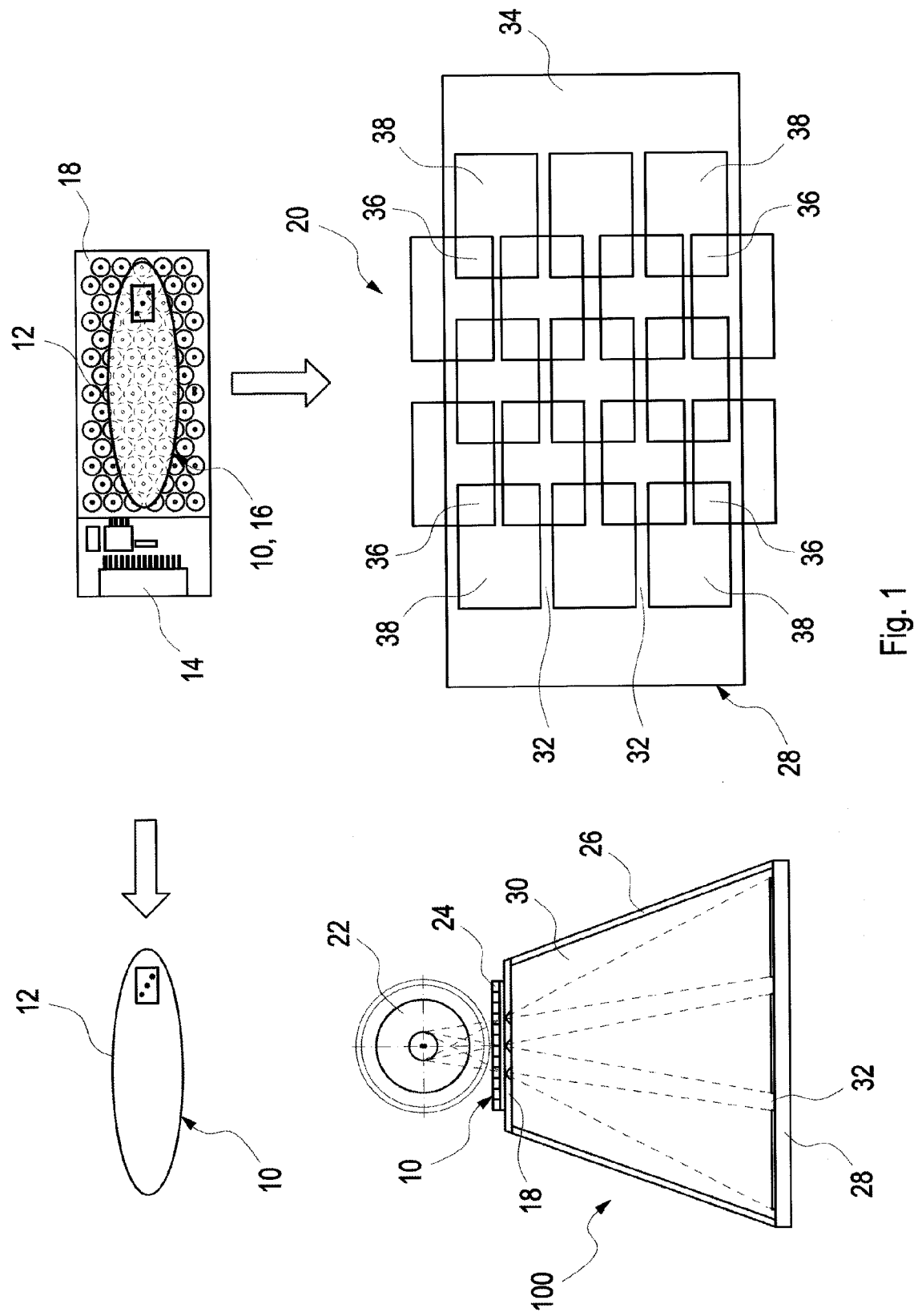
FIG. 1: schematic of an integrated optical detector and a SPECT camera with a multi-pinhole collimator.

An aspect of the present invention is a highly sensitive instrumentation system for identifying the location, magnitude, and time variation of specific functional or molecular events by simultaneously detecting optical and radioactive tracer and marker types in vivo. The inventive instrument is useful for monitoring functional events associated with, for instance, metabolism, physiological changes, and receptor binding, as well as for monitoring molecular events, such as gene expression and enzyme activity, which can be imaged and detected using the inventive SPECT/OT combination instrument.

An innovative aspect of the present invention is that it makes it possible to perform unified simultaneous acquisition, reconstruction, and tracer/probe-kinetic modeling for dual-modality optical and radiotracer small animal imaging without the drawbacks such as explained above. Use of this device in academic or research environments has the potential to foster interdisciplinary research that leads to new approaches of molecular imaging techniques, to the development of additional reporter constructs, and to a better understanding of the mechanisms of disease and response to therapy. The inventive application to small animal imaging can also be extended to imaging cancerous tissues, such as breast cancer, and melanoma by simple changes to the overall geometry of the systems.

An aspect of the present invention is the use of a plurality of specific detection cameras that are mounted on a common gantry to acquire images around a single axis of rotation with axially un-shifted, i.e. identical, spatially over-lapping field-of-views (FOV) of the involved sub-modalities. Thus, the overall sensitivity of the inventive imaging apparatus, which is one of the two critical parameters of in vivo imaging, is improved.

The invention solves the problem of single-procedural, simultaneous projection data acquisition and image reconstruction of (i) time-resolved in vivo distributions of single- or multi labeled low-energy (light) fluorescent or bioluminescence optical probes (OT), and (ii) high-energy (various radioisotopes) photon emitting (SPECT) molecular markers in a small object, particularly in mice and rats, but also in a specific human organs and tissues such as breast and skin, whereby both data types are acquired from identical projection angles, either with a single or, preferable, a multitude (most optimal four) of rotating dual-modality detector heads.

Fully integrated modalities (i) and (ii) employ specific detection cameras that are mounted on a common gantry (explained below) whereby projection images are acquired around a single axis of rotation with axially un-shifted (i.e. identical), spatially over-lapping field-of-views (FOV) of the involved sub-modalities.

Thus present invention resolves issues associated with separately imaging modalities (i) and (ii) (i.e. sequentially imaging the object with different devices) as for instance the direct study of tracer/marker kinetics, image registration, time resolved concurrent data analysis and animal handling which are inaccessible (kinetics) or become crucial (registration, animal management). Accordingly, the present invention proposes an instrumentation system that is highly sensitive in identifying location, magnitude, and time variation of specific functional (metabolism, physiological information, receptor binding, etc.) or molecular events (e.g., gene expression and enzyme activity) by simultaneously detecting optical and radioactive tracer and marker types in vivo.

The dual-modality instrument has been designed so that the optical modality detector is located in front of a SPECT modality collimator. The optical detector is separating and detecting low energy optical photons from the multi-energetic photon flux while high-energy SPECT photons are unaffected by this and, hence, are transmitted through the optical detector to be detected by the SPECT-detector which is located in radial extension to the optical detector.

In application, the invention performs non-invasive fully tomographic simultaneous image acquisition of dual-labeled (near-infrared) fluorescent, bioluminescence and high-energy photon emitting molecular and functional markers in small objects, particularly mice and rats, but also in specific human organs and tissues such as breast and skin. The invention solves problems connected to separately imaging targets with different devices, as for instance the direct study of tracer/marker kinetics, image registration, time-resolved concurrent data analysis and animal handling which are inaccessible (kinetics) or become crucial (registration, animal management). The invention assesses visual representation, characterization, and quantification of biological processes at the cellular and sub-cellular levels within intact living organisms by means of simultaneously performed image acquisition procedures. The invention proposes an instrumentation system that is highly sensitive in identifying location, magnitude, and time variation of specific molecular events (e.g., gene expression and enzyme activity) by simultaneously detecting above listed tracer and marker types in vivo.

The inventive imaging system is versatile and may be useful for a number of applications, including, but not limited to:
(i) imaging specific cellular and molecular processes, e.g. gene expression, or more complex molecular interactions such as protein-protein interactions,
(ii) monitoring multiple molecular events simultaneously;
(iii) tracking single or dual-labeled cells;
(iv) optimizing drug and gene therapy, to image drug effects at a molecular and cellular level;
(v) assessing disease progression at a molecular pathological level; and (vi) creating the possibility of achieving all of the above goals of imaging in a single, rapid, reproducible, and quantitative manner.

Further application-specific use is anticipated to monitor time-dependent experimental, developmental, environmental, and therapeutic influences on gene products in the same animal (or patient), to study the interaction of tumor cells and the immune system, to study viral infections by marking the virus of interest with a reporter gene, and others. There is also an enormous clinical potential for the noninvasive assessment of endogenous and exogenous gene expression in vivo (gene (DNA), message (RNA), protein, function), for imaging receptors, enzymes, transporters, for novel applications in basic and translational research (gene therapy, etc.), for early detection of disease, for guidance of therapeutic choices, for monitoring drug action, for aid of pre-clinical drug development, for non-invasive and repetitive monitoring of gene therapy, and for optimizing clinical trials of human gene therapy.

According to one aspect, the inventive apparatus therefore integrates an optical detector 10 and a SPECT camera 28 which employs a multi-pinhole collimator 18. FIG. 1 shows an optical detector 10 having a field of view which is identified by reference numeral 12. Behind the optical detector 10, a multi-pinhole mask 18 is arranged. A read-out electronics is labeled with reference numeral 14. In FIG. 1, a view 16 in the drawing plane is shown in which the optical detector 10 is arranged in front of said multi-pinhole mask labeled with reference numeral 18. Still further, the inventive apparatus comprises a SPECT-detector 28 shown in the plane 34. Rectangular areas 38 of the surface of said SPECT-detector 28 are separated from one another by thin spaces identified with reference numeral 32 in FIG. 1. An overlap 36 shows single areas 38 of said SPECT-detector 28 covering respective edges of other single areas 38 on the surface of the SPECT-detector 28. That optical detector 10 is arranged above said SPECT-detector 28. For instance, in one embodiment of the present invention, said optical detector 10 is arranged on top of a shielding 26, whereas said SPECT-detector 28 is arranged on the bottom of said shielding 26. Said shielding 26 defines a hollow interior 30. Below said optical detector 10, the surface of which is labeled with reference numeral 24, said multi-pinhole mask 18 is arranged in this part integrated into the ceiling of said shielding 26. Above said surface 24 of the optical detector 10, an imaged object 22 is shown, the radiation beams are given in dotted lines. Reference numeral 100 depicts the entire optical detector unit.

Figure 2:
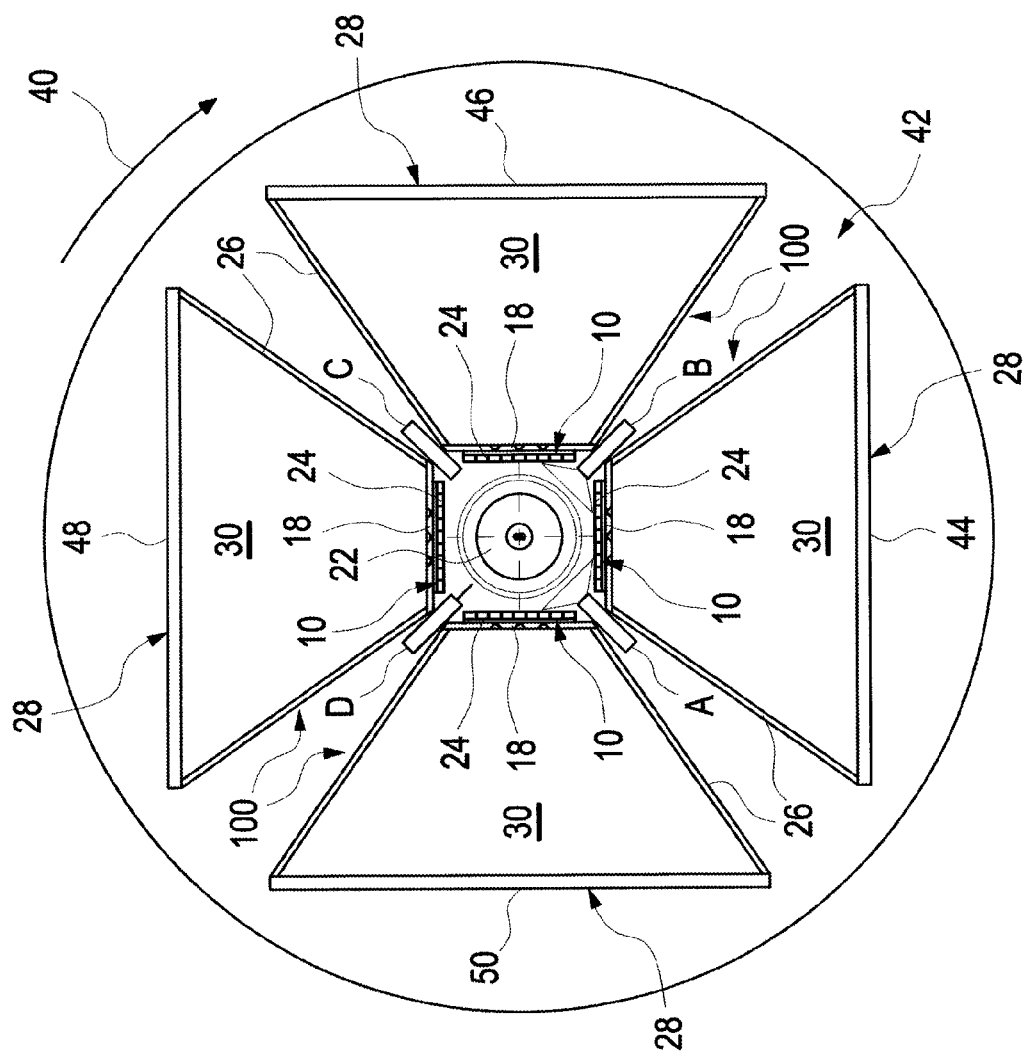
FIG. 2: schematic of a plurality of combined SPECT-OT detectors on a common gantry, the collimator of the SPECT system being a multi-pinhole type. Laser scanning and large-field light sources are integrated into the inventive apparatus to facilitate fluorescence and bioluminescence imaging.

Laser scanning and large-field light sources are integrated to facilitate fluorescence imaging in addition to bioluminescence imaging. FIG. 2 shows a schematic of a plurality of combined SPECT-OT detectors on a common gantry, a collimator of a SPECT system being a multi-pinhole type. According to this arrangement, laser scanning and large field light sources are integrated into the inventive apparatus to facilitate fluorescence and bioluminescence imaging. As can be seen in FIG. 2, four optical detector units 100 are arranged on a common gantry 42, which is rotatable into sense of rotation indicated by arrow 40. Four optical detector units 100 each having a SPECT-detector 28, said shielding 26 and a multi-pinhole mask 18 arranged below the optical detectors 10 are provided. According to the embodiment given in FIG. 2, said optical detector units 100 are arranged within an angle of 90° with respect to one another, thus, completely surrounding said imaged object 22. Four light sources A, B, C, D are provided between the respective shielding 26 of two neighboring optical detector units 100 arranged adjacent to one another. As can be seen in FIG. 2, said second light source B and said first light source A each emit light directed to said imaged object 22 being surrounded by the optical detectors 10. Corresponding to FIG. 1, below each of said optical detectors 10 said multi-pinhole mask 18 is arranged within the shielding 26 of each of the optical detector units 100. Said SPECT-detectors 28 are preferably dual modality detector heads being a part of each optical detector unit 100. Each optical detector unit 100 comprises four dual modality heads labeled 44, 46, 48, 50 according to FIG. 2. Each optical detector unit consists of a large-area photo sensor for light detection, a micro lens array for field of-view definition, a septum mask for cross-talk suppression, and a transferable filter for wavelength selection.

Figure 7:
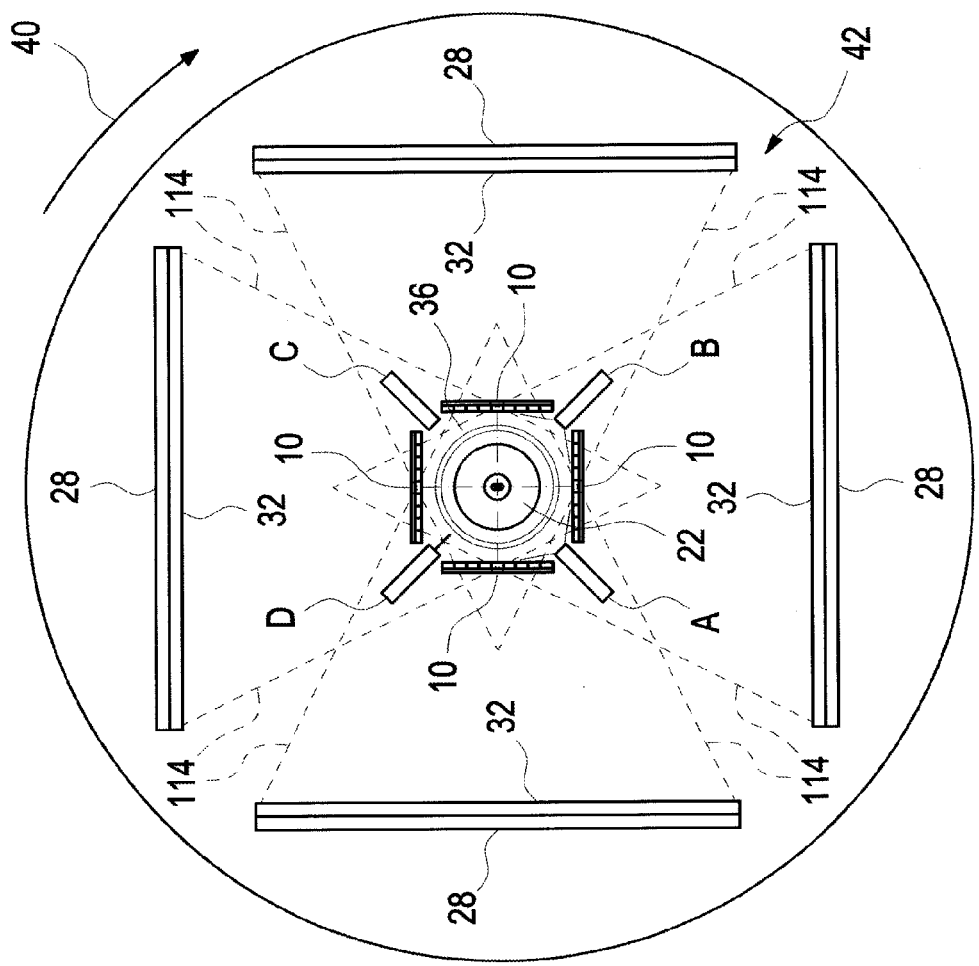
FIG. 7: schematic of a plurality of combined SPECT-OT detectors on a common gantry, the collimator of the SPECT system being a fan-beam type. Laser scanning and large-field light sources are integrated into the inventive apparatus to facilitate fluorescence and bioluminescence imaging.

In one design, optical photons are separated from the photon flux and collimated onto a detector by a cylindrical lattice of micro lens arrays 92 (see FIG. 4) (MLAs), which form an inner optical detection ring while a SPECT-detector 28 is mounted in radial extension. In one embodiment of the present invention, an optical detector 10 may be mounted onto the surface of the SPECT collimator 94 (see FIG. 4). The inventive apparatus can accommodate the incorporation of different collimators 94, and in that set-up the optical detector 10 may be located most effectively close to the imaged object 22 while the SPECT camera is be positioned further away from the imaged object 22, depending on field-of-view geometry 114. See, for instance, an example of such an arrangement in FIG. 7. Thus, multiple cameras can be mounted on a common gantry 42 as illustrated in FIGS. 2 and 7, respectively. In addition to the four detector heads 44, 46, 48, 50 there also are included, for instance, four light sources, which are necessary for fluorochrome excitation, labeled A to D in FIGS. 2 and 7, respectively. By way of example, sources A and B are bright-field sources, source C is not producing light, and source D is producing a light beam for focal point illumination.

FIG. 3 shows the apparatus and results of a study illustrating the improvement of the performance of the SPECT-detector 28 if multi-pinhole collimators 18 are used. Shown are the results for 1, 4, and 6 pinholes with regard to efficiency (sensitivity). Said optical detector unit 100 comprises the SPECT-detector 28, the surface of which is labeled by reference numeral 32. Said optical detector unit 100 comprises the shielding 26 on top of which the multi-pinhole mask 18 is arranged. A distance b shows the distance between the surface of said multi-pinhole mask 18 and the imaged object 22. In the diagram according to FIG. 3, the efficiency is shown with respect to the spatial resolution given in mm. According to the diagram, a poor third efficiency 80 is achieved by a multi-pinhole mask 18 having one pinhole only. An increase in the number of pinholes results in an improvement of efficiency such as the second efficiency 70 when four pinholes are provided in said multi-pinhole mask 18. A good first efficiency is obtained, see reference numeral 60, if said multi-pinhole mask 18 comprises six pinholes. The larger the number of pinholes the better the efficiency is. That is the result of the diagram according to FIG. 3.

According to FIG. 4, a single optical detector system comprises four parts: (1) a micro lens array 92 intended for field-of-view definition, (2) a large area complementary metal oxide semiconductor (CMOS) chip for light detection, (3) a septum mask for cross-talk suppression, and (4) exchangeable filters 90 for wavelength selection.

The assembly of all parts allows for a very thin detector design yielding an effective complete detector thickness of about 4.0 mm. Optical imaging using micro lens arrays 92 (MLAs) also referred to as microlenticular or lens let arrays are used primarily in optical data communication applications, e.g. to interconnect optical fiber bundles, or as light collection elements to increase the optical fill factor in CCDs. See FIG. 4, which shows a rendering of the cross-sectional view of the optical detector 10 along with a photograph of the various parts of the detector 10. See also WO2006111486, which is incorporated herein by reference. According to the cross-sectional view of the optical detector 10 according to FIG. 4, said optical detector 10 comprises an exchangeable filter 90, said micro lens array 92, previously being mentioned as well as a collimator 94. Still further, a photosensor 96 and a corresponding electronics 98 are comprised within the optical detector 10. Since all components of said optical detector 10 are very thin, the effective complete detector thickness can be minimized and as previously mentioned amounts to about 4 mm.

To date, MLAs 92 are produced from fused silica, silicon, or other materials, depending on application wavelength, and are typically available in array sizes up to 120 mm×120 mm and with lens diameters in the range of 10 microns to 2 mm. In the field of optical imaging, micro lens arrays 92 have been used for instance to realize an artificial apposition compound eye, as described recently by Duparr'e and colleagues. In the device concept presented herein, the MLA 92 is used exclusively for field-of-view definition allowing for non-contact in vivo optical imaging and possibly optical tomography. An analogy for illustrating the purpose of the micro lens array in this application might be seen in the use of multi-hole collimators in high-energy detector physics such as in SPECT.

To allow imaging of whole mice, it was found that planar optical projection images should cover an effective area of about 10 cm axially×5 cm transaxially. Tomographic data can potentially be acquired either by rotating a single detector 10 around the object 22 or by mounting a multitude of detectors 10 on a common gantry 42. Four detectors 10, as shown in FIG. 2, i.e. reference numerals 44, 46, 48, 50, having the above mentioned dimensions potentially allow for simultaneous tomographic optical imaging.

In order to study intrinsic spatial resolution and sensitivity of the optical detector unit 100 an imaging apparatus was used in two different experimental settings. Intrinsic spatial resolution 108.1 to 108.8 according to FIG. 5 as a function of object-detector distance d was measured using an electroluminescent light screen (El-Light, Strausberg, Germany), 10 cm×10 cm in size, transilluminating a pattern of circles, ranging in diameter from 1.0 mm up to 2.0 mm in 0.2 mm steps, compared in whole diameters 104.0 to 104.5 according to FIG. 5, similar to the well-known Derenzo-like phantom geometry. Detector sensitivity with respect to d was investigated using a red light emitting diode (Kingbright DLA2/6ID, Kingbright Elec. Co., Ltd., Taipei Hsien, Taiwan) powered by a constant current source in the pico-Ampere range.

In this setup, source intensity can be precisely controlled by altering the forward current. Note that in all experiments conducted the maximum forward current applied was 60 pA which yields a light output that is hardly human-perceivable. In order to further judge detector sensitivity images were additionally acquired using a highly sensitive CCD camera (Orca-AG, Hamamatsu Photonics K. K., Hamamatsu City, Japan). It employs a cooled advanced progressive scan interline CCD chip with 1344×1024 pixel resolution and is rated at 0.1 electrons per second dark current (at −20° C.), 8 electrons read noise, 18,000 electrons saturation, 12 bits digitization accuracy. A 4×4 binning was used in all experiments. The camera was equipped with a Cinegon 1.4/18 lens (Schneider Optische Werke GmbH, Bad Kreuznach, Germany). Exposure time was set to 30 sec for all measurements, involving the CCD as well as the CMOS sensor.

Figure 5:
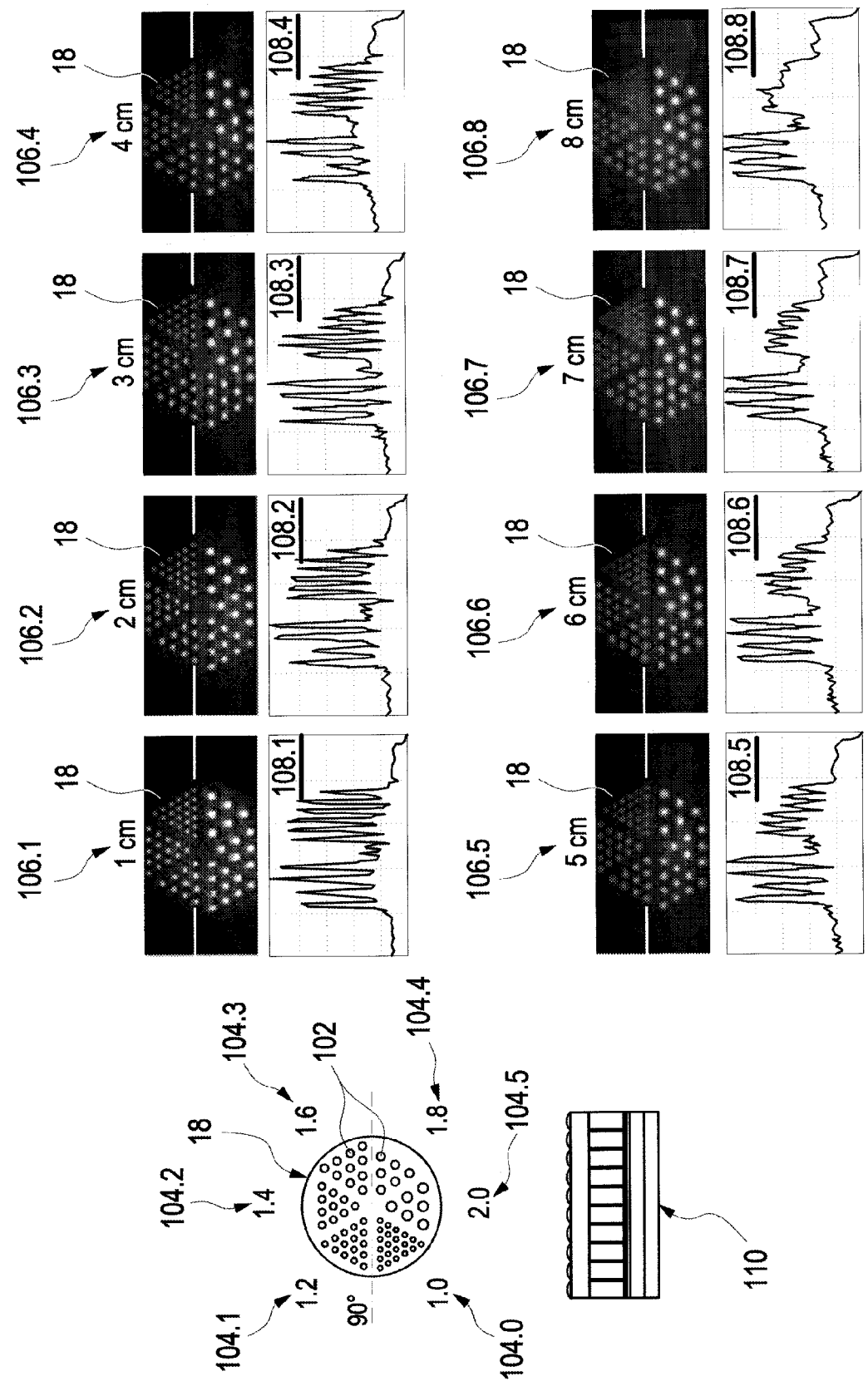
FIG. 5: shows the results of a phantom data acquisition study performed to assess the imaging characteristics of the optical detector as used in this implementation of dual modality SPECT-OT imaging.

FIG. 5 shows the results of a phantom data acquisition study which was performed to assess the imaging characteristics of the optical detector 10 as used in this implementation of dual modality SPECT-OT imaging.

According to FIG. 5, the distance d between object and detector has been varied between a first detector-object distance 106.1 of 1 cm in 1 cm steps until an object-detector distance of 8 cm, see reference numerals 106.8. The steps in between have been made within an 1 cm range, compare reference numerals 106.2, 106.3, 106.4, 106.5, 106.6 and 106.7, respectively. Corresponding to said variations in the object-detector distance intrinsic spatial resolutions 108.1 to 108.8 have been measured. The arrangement of pinholes 102 on the multi-pinhole mask 18 according to FIG. 5 has been unaltered, the variation between object and detector has varied. Compared with the first distance 106.1 of 1 cm between object and distance with the setting of a distance 106.8 of 8 cm and comparing both intrinsic spatial resolutions 108.1 and 108.8, respectively, the intrinsic spatial resolution 108.8 is more trapezoidal as compared to the very distinct intrinsic spatial resolution 108.1 of the first set-up having a distance 106.1 of 1 cm between detector and object.

In order to study the multi-pinhole geometry, a Monte Carlo simulation study was performed. FIG. 6 shows the result of Monte Carlo simulations that have been performed in order to investigate the multi-pinhole setup as well as possible effects the optical sensor might have on the SPECT photons. There were no measurable degradations found as a result of the optical detector 10 being within the field-of-view 114 of the SPECT camera.

A variety of suitable large-field photo-sensors are available commercially, most of them incorporating either CCD or CMOS sensors which are two different technologies for capturing images digitally by converting light into electric charge. In a CCD sensor, every pixel's charge is transferred through a single output node, voltage-converted, pre-amplified, buffered, and sent off-chip as an analog signal with comparatively low noise, high dynamic range, and high uniformity. In a CMOS sensor, each pixel has its own charge-to-voltage conversion, and most CMOS sensors also include amplifiers, noise-correction, and digitization circuits. CMOS sensors have improved considerably in achievable dynamic range and signal-to-noise ratio and start to challenge CCDs in terms of spatial resolution and sensitivity.

The assembly as presently described employed a RadEye™ 1 large-area CMOS imaging sensor (Rad-icon Imaging Corp., Santa Clara, Calif.). Another favorable feature of this sensor is the lateral placement of the read-out electronics 14, 98 which can be placed outside the field-of-view 114 of the SPECT subsystem and such can be shielded to avoid radiation damage. The sensor chip is equipped with a 512× 1024 silicon photodiode matrix at 48 μm pixel pitch, yielding a 24.6 mm×49.2 mm active area. These sensors can be positioned head-to-head leaving only a small gap of less than 1 mm between sensor fields such that active areas of 10 cm× a manifold of 2.5 cm can be constructed. According to the manufacturer's data sheet the sensor can be operated at frame rates of 0.01 to 4.5 per second and has a dynamic range of 85 dB (14 bits). Average dark current is stated with 4,000 electrons per second (at 23° C.) and the read noise with 150 electrons (at 1 frame per second). Saturation is attained at 2,800,000 electrons per pixel. The detector signal is transferred to a PXD1000 digital frame grabber (CyberOptics Semiconductor Inc., Beaverton, Oreg.).

While sensitivity is of foremost concern for in vivo imaging applications the need for highest intrinsic spatial resolution of the optical detector 10 might be less important because spatial resolution is primarily limited by photon scattering in tissue and not so much by the intrinsic spatial resolution of the detector-an inverse situation as compared to SPECT.

MLA's 92 size and lens geometry was specified according to the parameters of the CMOS sensor as lens pitch g should be a multiple of pixel pitch, and also with respect to the desired intrinsic spatial resolution (ISR) of the optical imager. For the intended in vivo imaging application ISR is considered necessary to be in the range of about half a millimeter. Given 48 µm pixel pitch of the CMOS sensor we did chose MLA lens pitch at 480 µm. Hence, individual lenses on the MLA correspond to local fields of 10×10 sensor pixels. The overall size of the MLA is 24.6 mm×49.2 mm, matching the size of CMOS sensor. MLAs were manufactured according to our specifications by Advanced Microoptic Systems GmbH, Saarbruecken, Germany using S-TIH53 optical glass (Ohara Inc., Kanagawa, Japan) of 1 mm thickness. Focal lengths of all lenses have been defined at 2.2 mm forming a focal plane at that distance coplanar to the MLA at which the large-field CMOS sensor is aligned.

In order to avoid cross-talk between the outputs of individual lenses, a light-tight, non-reflective septum mask (similar in structure to a parallel-hole collimator in SPECT) is placed between the CMOS sensor and the MLA 92. Bore diameter is chosen at 400 µm with 480 µm pitch, which is identical to lens pitch. This mask was coaligned with the lens pattern. Having the same overall size as sensor and MLA its thickness is defined by the empty space (=focal distance minus some offset) between MLA and sensor, which is 2.1 mm. The final element of the arrangement is a removable filter 90 located in front of the MLA 92 used to filter the optical signal. In our realization, the filter 90 and its bearing are also used to protect the detector from fluid contamination.

In connection with FIG. 6 it has to be mentioned that said shielding 26 of the optical detector unit 100 comprises said SPECT-detector 28 and on its upper sealing below the multi-pinhole mask 18 the optical detector 10. The surface 24 of said optical detector 10 is directed towards the imaged object 22. As shown in FIGS. 1 and 2, respectively, said shielding 26 limits the hollow interior 30 of the optical detector unit 100. FIG. 6 shows the results of a Monte Carlo simulation 10,000,000 photons, 140.5 keV, rdi lesions: background (1:1:1): 0 (left hand side)/20 (right hand side).

According to FIG. 7, a plurality of combined SPECT-OT detectors 28 are arranged on a common gantry 42 which is rotatable in the sense of rotation 40. The collimators of this SPECT system each are of fan beam type. Laser scanning and large field light sources A, B, C and D, respectively are integrated to provide for fluorescence and bioluminescence imaging.

The arrangement according to FIG. 7 resembles the arrangement according to FIG. 2, the difference being that said SPECT-detectors 28 having surfaces 32 oriented to the imaged object 22 with shieldings 26. Said SPECT-detectors 28 are of fan beam type, the respective field of view indicated by reference numeral 114. Said beams overlap within the area of the imaged object 22 where the optical detectors 10 between which said light sources A, B, C and D, respectively, are arranged.

REFERENCE LIST

10 Optical detector
12 Field of view of optical detector
14 Read-out electronics
16 Front-view
18 Multi-pinhole mask
20 Field of view mapping
22 Imaged object
24 Surface of optical detectors
26 Shielding
28 SPECT-detector
30 Hollow interior
32 Surface of SPECT-detector
34 Plane
36 Overlap
38 Area
40 Sense of rotation
42 Gantry
44 Dual modality head 1
46 Dual modality head 2
48 Dual modality head 3
50 Dual modality head 4
A 1. light source
B 2. light source
C 3. light source
D 4. light source
b Distance
60 1. efficiency (6 pinholes)
70 2. efficiency (4 pinholes)
80 3. efficiency (1 pinhole)
90 Filter
92 Microlens array
94 Collimator
96 Photosensor
98 Electrons
100 Optical detector unit
102 Pinholes
104.0-104.5 Pinhole diameter
106.1-106.8 Detector-object distance
108.1-108.8 Intrinsic spatial resolution
110 Layered structure
112 Pinhole area
114 Field of view of collimator

The invention claimed is:

1. A dual-modality imaging system, wherein at least one single photon emission computed tomography (SPECT) camera for acquiring SPECT data and at least one optical imaging detector for acquiring optical imaging data are arranged to acquire the SPECT data and the optical imaging data of an imaged object simultaneously and from the same projection angle, the at least one optical imaging detector being a non-contact optical imaging detector for bioluminescence, fluorescence, and reflectance imaging and wherein the SPECT sub-system apparatus comprises a SPECT-detector to which a collimator is attached for high-resolution/high-sensitivity radio-nuclide imaging and at least one optical imaging detector being arranged within the imaging volume to detect photons emitted by the imaged object, characterized in that the at least one optical imaging detector comprises a micro-lens array with a plurality of micro-lenses, the optical detector being attached onto the surface of the collimator of the SPECT system.

2. The dual-modality imaging system according to claim 1, wherein the SPECT camera collimator is a single-pinhole type, or is a multi-pinhole type, or is a parallel beam type, or is a fan-beam type, or is a con-beam type, or is an astigmatic collimator type, or is any parallel, diverging, or converging multi-hole type, or is an converging type with a single or multitude of focal points or lines.

3. The dual-modality imaging system according to claim 1, wherein at least a subsystem of the optical imaging detector is permanently attached at the imaged object facing front of the collimator of the SPECT apparatus or which is removable combined with the collimator of the SPECT apparatus.

4. The dual-modality imaging system according to claim 1, wherein the at least one optical imaging detector comprises at least one photo detector.

5. The dual-modality imaging system according to claim 1, wherein the at least one optical imaging detector comprises a position-sensitive photo detector.

6. The dual-modality imaging system according to claim 5, wherein the at least one optical imaging detector comprises a micro-lens array and the position-sensitive photo-detector is positioned at the focal plane of a micro-lens array.

7. The dual-modality imaging system according to claim 5, wherein the position-sensitive photo-detector is at least one sensor selected from the group of charge-coupled device (CCD) based detector, avalanche photo diode (APD) array, photo diode array or complementary metal-oxide semiconductor (CMOS) sensor.

8. The dual-modality imaging system according to claim 1 wherein at least one combination of the SPECT-detector and the optical imaging detector is mounted on a common gantry which is rotatable around 360 degrees to allow for arbitrary radial positioning of the optical detector(s) and of the SPECT camera(s) and to allow for tomographic imaging.

9. The dual-modality imaging system according to claim 1, further comprising a single or plurality of light sources for illuminating the imaged object.

10. The dual-modality imaging system of claim 1, wherein the collimator is a multi-pinhole type collimator.

* * * * *